United States Patent [19]

Nobbio

[11] Patent Number: Plant 6,093

[45] Date of Patent: Feb. 2, 1988

[54] CARNATION NAMED MEI CHENG

[75] Inventor: Giacomo Nobbio, San Remo, Italy

[73] Assignee: Klemm & Sohn, Stuttgart-Muhlhausen, Fed. Rep. of Germany

[21] Appl. No.: 798,303

[22] Filed: Nov. 15, 1985

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler; W. Dennis Drehkoff

[57] ABSTRACT

A new, hybrid carnation, distinguished by its profuse production of Tyrian Purple flowers of medium size, each petal of which is bordered with a ruffled margin of a light color, approaching white, the flowers being borne singly on strong, upright pedicels, which are carried on sturdy, upright peduncles about 45-60 cm. long.

1 Drawing Figure

BACKGROUND OF THE NEW PLANT

This new carnation originated at San Remo, Italy as a seedling derived by my crossing plants selected from breeding stock maintained in my greenhouse at San Remo, Italy, the object of this crossing being the production of an improved carnation suitable for cut-flowers. In 1981, it was discovered that the plant possessed the precocity and color contrast that I was seeking. Asexual propagation of this new plant, by means of cuttings, has been carried out at Stuttgart, West Germany, and San Remo, by me and under my direction through successive generations and the distinctive characteristics of this plant has been found to hold true from generation to generation and appear to be firmly fixed.

DESCRIPTION OF THE DRAWING

My new variety of carnation plant is illustrated by the accompanying full color photographic drawing, which shows a group of flowering stems having buds in various stages of opening, newly opened flowers and blooms in further stages of maturity, the flower coloration being shown as nearly true as it is reasonably possible to obtain by means of conventional photographic procedures.

DESCRIPTION OF THE NEW PLANT

The following is a detailed description of my new carnation variety, based upon observation of the plants grown under conventional greenhouse practices, with color designations being according to the Horticultural Colour Chart published by The British Colour Council in collaboration with The Royal Horticultural Society of London, England.

THE PLANT

Origin: Seedling.
Parentage:
- *Seed parent.*—Breeding Stock Number 821; Pollen.
- *Parent.*—Breeding Stock Number 719.

Classification:
- *Botanic.*—*Dyanthus caryophyllus.*
- *Commercial.*—Greenhouse carnation.

Form: Bush.
Height: About 90 to 110 cm.
Growth: Upright.
Strength: Moderate.

Branching: Normal.
Foliage:
- *Quantity.*—Moderate.
- *Leaf size.*—Small.
- *Leaf shape.*—Oblong.
- *Margin type.*—Entire.
- *Texture.*—Smooth.
- *Color.*—Upper side — dark green; Under side — dark green.

THE BUD

Size: Medium, about 15 mm. in diameter and about 25 mm. long.
Form: Cylindrical.
Shape: Ovoid.
Opening rate: Moderate.
Calyx:
- *Size.*—Small.
- *Length.*—About 2 cm.
- *Shape.*—Cylindrical.
- *Splitting.*—The calyx does not split.
- *Aspect.*—Smooth.

Sepals:
- *Number.*—Up to eight.
- *Condition.*—Upstanding.
- *Color.*—Inside — light green; outside — gray green.

THE FLOWER

Blooming habit: Continuous and profuse.
Size of the bloom: Medium.
- *Diameter.*—About 5-6 cm.
- *Depth.*—About 3-4 cm.

Borne: Singly.
Shape: Flat at first opening and the form does not change as the flower matures.
Petalage:
- *Number of petals.*—About 40-45.
- *Arrangement.*—Generally imbricated.
- *Form.*—Slightly serrated and ruffled.
- *Texture.*—Soft.
- *Appearance.*—Velvety.
- *Color.*—Outer petals: H.C.C. 727 in the main body with margins of a light color approximating white.

Peduncle: Upright.
- *Length.*—About 45-60 cm.

*Color.*—Deep green.

*Persistence.*—The flowers hang on and dry; the bloom stays upright.

*Fragrance.*—None.

*Lasting quality.*—On the plant, ten days; as a cut flower, eight days.

REPRODUCTIVE ORGANS

Stamens:

*Number.*—About 8 to 12.

Anthers:

*Color.*—Gray.

Filaments:

*Length.*—0.6 to 0.8 cm.

*Color.*—White.

Pollen:

*Color.*—Gray.

Pistils:

*Number.*—Two to three.

Styles:

*Length.*—0.6 to 0.8 cm.

*Color.*—White.

Stigmas:

*Color.*—White.

Fruit: Fertile in summer.

*Shape.*—Ovoid.

*Color.*—At maturity — green/brown.

This new variety of carnation plant is particularly distinguished by the Tyrian Purple coloring of its flowers which have petals with a ruffled and undulated margin, light in color, approximating white, and which are borne on erect pedicles. The flower has an excellent capacity for profuse production of blooms which is essential for the cut flower market.

I claim:

1. A new and distinct variety of carnation plant, substantially as herein shown and described, characterized by its high productivity of Tyrian Purple flowers borne singly on upright pedicles, the flowers being characterized by having petals which have a ruffled margin of a light color, approximating white.

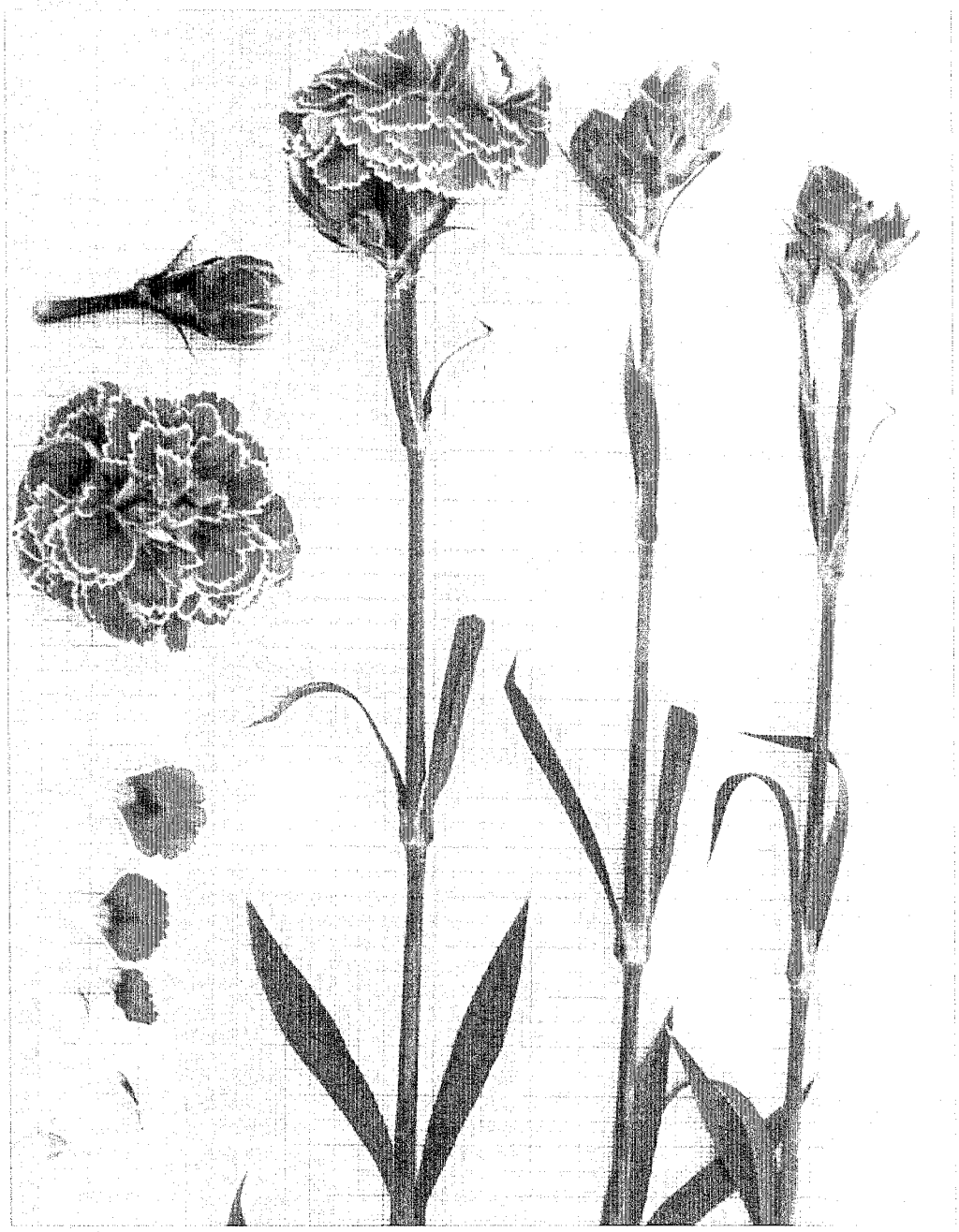

* * * * *